Figure 1:
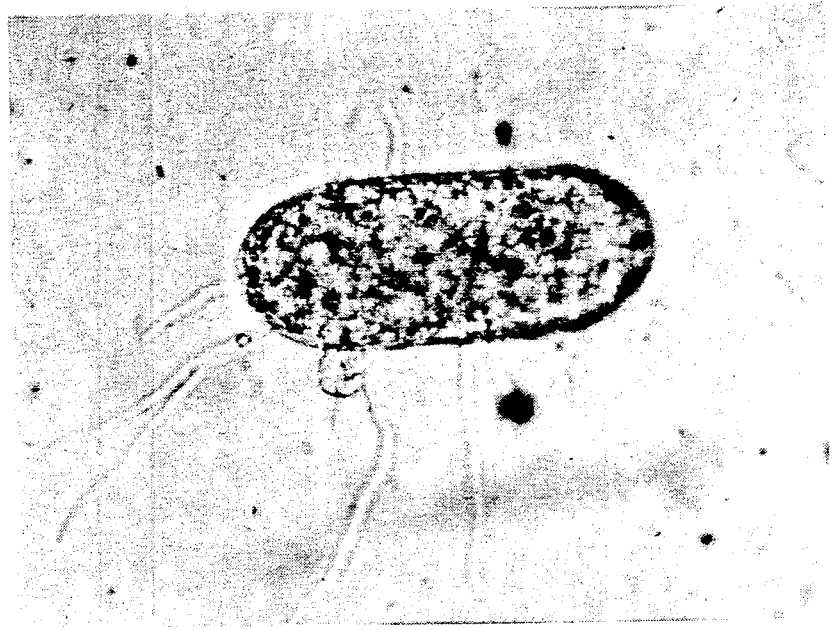

United States Patent [19]

Riggs et al.

[11] Patent Number: 5,019,389
[45] Date of Patent: May 28, 1991

[54] METHOD OF CONTROLLING CROP AND PLANT PESTS

[75] Inventors: Robert D. Riggs; Dong G. Kim, both of Fayetteville, Ak.

[73] Assignee: University of Arkansas, Fayetteville, Ak.

[21] Appl. No.: 257,505

[22] Filed: Oct. 13, 1988

[51] Int. Cl.$^5$ ............................................. A01N 63/00
[52] U.S. Cl. ................................ 424/93; 424/DIG. 8; 424/DIG. 10
[58] Field of Search ........... 424/93, DIG. 8, DIG. 10

[56] References Cited

PUBLICATIONS

Kim et al., Control of Heterodera Glycines by a Fungus Parasite, Journal of Nematology, vol. 19, 26th Annual Meeting, 535.

*Primary Examiner*—John W. Rollins
*Attorney, Agent, or Firm*—Hill, Van Santen, Steadman & Simpson

[57] ABSTRACT

A method of controlling crop pests and parasites is provided. The method includes the step of treating a crop with a sufficient quantity of Arkansas Fungus 18-A so as to control the pests. A substantially pure culture of Arkansas Fungus 18-a is also provided.

11 Claims, 2 Drawing Sheets

METHOD OF CONTROLLING CROP AND PLANT PESTS

BACKGROUND OF THE INVENTION

The present invention relates generally to a method for controlling crop and plant pests and parasites. More specifically, the present invention relates to a method of controlling nematodes that invade soybean and like crops.

There are many nematodes and like pests and parasites that invade and damage plants and crops. An example of such a pest is *Heterodera glycines*. Other such pests include, for example, *Meloidogyne incognita* and *Heterodera schachtii*.

*Heterodera glycines* nematodes are parasites, or pests, that feed on soybean crops. These nematodes result in stunting, and yellowing, and reduce yield in typical soybean crops. Attempts to control the nematodes have not been entirely successful. One method for attempting to control the nematodes is to use a chemical soil treatment. The known chemical treatments, however, do not function entirely satisfactory in controlling the nematodes and are very expensive. An alternative method for attempting to control *Heterodera glycines* nematodes is through crop rotation. But, for many farmers, crop rotation is not a viable alternative as many crops do not have the yield of soybeans.

Accordingly, there is a need for a method of controlling *Heterodera glycines* and like nematodes.

SUMMARY OF THE INVENTION

The present invention provides a method for controlling pests and parasites in crops. The invention is particularly directed to a method for controlling *Heterodera glycines* in soybean fields.

The method of the present invention comprises the steps of treating a crop with a composition including a substantially pure culture of Arkansas Fungus 18-A in a sufficient quantity to control nematodes that may be present on the crop or in the soil. The fungus parasitizes the eggs and females of the nematodes. Pursuant to the present invention, a substantially pure culture of Arkansas Fungus 18-A is prepared and can be placed in a vehicle that will allow it to control nematodes.

In an embodiment of the method, the invention comprises the method of treating a soybean crop with Arkansas Fungus 18-A in a sufficient quantity to control any *Heterodera glycines* that may be present on the crop or in the soil.

In an embodiment, the method includes the step of applying the Arkansas Fungus 18-A in pellet form.

In an embodiment, the method includes the step of applying the Arkansas Fungus 18-A by placing the fungus in an irrigation water supply.

In an embodiment, the method of the present invention includes the step of preparing a substantially pure culture of Arkansas Fungus 18-A on an agar. The Arkansas Fungus 18-A can then be combined with a suitable vehicle to allow it to be delivered to a crop or plant.

The present invention also provides a method for controlling *Meloidogyne incognita* and *Heterodera schachtii*.

Additional features and advantages of the present invention will be apparent from the detailed description of the presently preferred embodiments and from the drawings.

BRIEF DESCRIPTION OF THE DRAWINGS

FIG. 1 is a photomicrograph of an egg of *Heterodera glycines* showing haustorium and early stage of infection by Arkansas Fungus 18-A.

FIG. 2 is a photomicrograph of an egg of *Heterodera glycines* showing advanced stage of infection by Arkansas Fungus 18-A.

FIG. 3 is a photomicrograph of a young female of *Heterodera glycines* infected by Arkansas Fungus 18-A.

DETAILED DESCRIPTION OF THE PRESENTLY PREFERRED EMBODIMENTS

The present invention provides a method for controlling nematodes and like pests on crops and/or plants. More specifically, the present invention provides a method for controlling *Heterodera glycines, Heterodera schachtii*, and *Meloidogyne incognita* on plants and crops. In a particular embodiment, the present invention provides a method for controlling soybean parasites, specifically *Heterodera glycines*.

To this end, the present invention provides a method for treating crops and/or plants with a fungus that functions to control nematodes and like pests on crops and/or plants. The fungus of the method of the present invention has been found to particularly parasitize the eggs and female of *Heterodera glycines*. The fungus of the method of the present invention is a mycelium fungus. A substantially pure culture of the fungus is maintained in the Plant Science Building at the University of Arkansas under the designation Arkansas Fungus 18-A. As used in this patent application, Arkansas Fungus 18-A refers to this particular fungus.

The inventors have satisfactorily grown a substantially pure culture of the Arkansas Fungus 18-A on artificial media. For example, a substantially pure culture of the Arkansas Fungus 18-A has been grown on potato dextrose agar and on pea juice agar. A substantially pure culture of the Arkansas Fungus 18-A has been grown at 25° C. on cornmeal agar. The substantially pure culture of the Arkansas Fungus 18-A has been grown on cornmeal agar at 25° C. through a wide pH range.

On agar, the substantially pure culture of the Arkansas Fungus 18-A produces sclerotium-like structures but does not produce spores. When egg-filled nematode cysts are placed in the presence of the Arkansas Fungus 18-A, either on agar or soil, the cysts are invaded and the eggs inside parasitized, i.e., the Arkansas Fungus 18-A penetrates the egg and consumes the contents of the egg as it grows.

The Arkansas Fungus 18-A, pursuant to an embodiment of the method of the present invention, can be used to control *Heterodera glycines* in soybean crops. The Arkansas Fungus 18-A can also be used to control *Meloidogyne incognita*, which probably is the most destructive plant parasitic nematode worldwide. The Arkansas Fungus 18-A can also be used to control *Heterodera schachtii* a parasite of the sugar beet.

Referring to the Figures, photomicrographs of diseased eggs and females of soybean-cyst nematode, *Heterodera glycines* are provided. The nematodes illustrated in the photomicrographs have been parasitized by a substantially pure culture of the Arkansas Fungus 18-A of the present invention. The ultrastructure of *Heterodera glycines* cysts, eggs, and juveniles parasitized by a substantially pure culture of the Arkansas Fungus 18-A were also studied using transmission electron microscopy (TEM) and scanning electron microscopy (SEM).

Using TEM, sections were taken of infected cysts that had abundant hyphae inside eggs and in unhatched juveniles. The TEM photomicrographs demonstrated that the cuticles of the cysts, egg shells, and juveniles were penetrated directly by the hyphae. It was found that internal hyphae often reemerged through the cuticle. The electron-dense substance evident at the site of hyphal penetration of the cyst cuticle was suggestive of localized enzymatic dissolution of the cutin layer.

SEM photomicrographs illustrated that the surface of infected eggs undulated greatly. This created a large number of furrows suggesting that the entire contents of the invaded eggs were replaced with mycelium.

Figure 2:
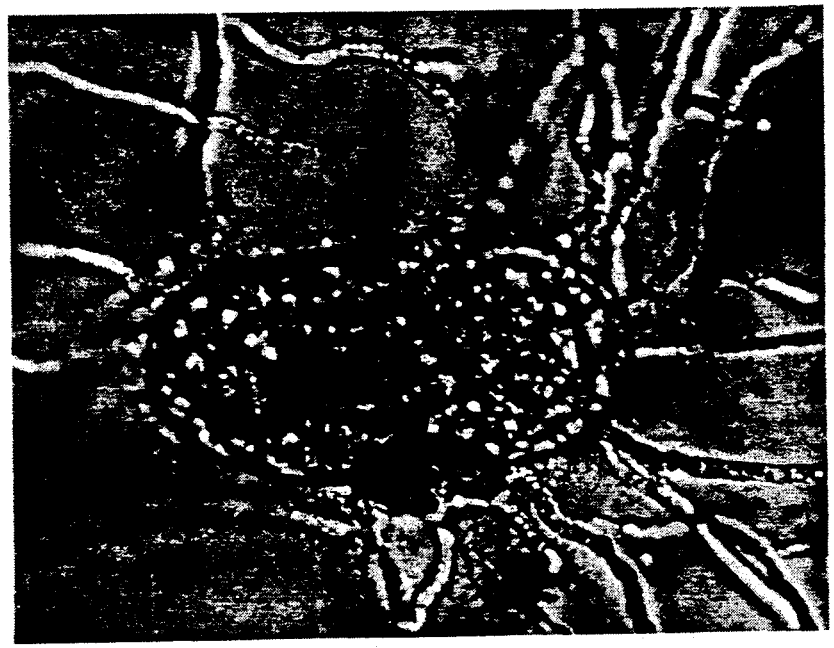
Figure 3:

FIG. 1 is a photomicrograph of an egg of *Heterodera glycines* showing haustorium and early stage of infection by a substantially pure culture of Arkansas Fungus 18-A. FIG. 2 is a photomicrograph of an egg of *Heterodera glycines* showing an advanced stage of infection by a substantially pure culture of Arkansas Fungus 18-A. FIG. 3 is a photomicrograph of a young female of *Heterodera glycines* infected by a substantially pure culture of Arkansas Fungus 18-A.

By way of example, and not limitation, examples of the present invention will now be given.

A substantially pure culture of the Arkansas Fungus 18-A was grown at 25° C. on cornmeal agar. The Arkansas Fungus 18-A was found to parasitize the *Heterodera glycines* eggs and cysts that were placed on the agar. The Arkansas Fungus 18-A was also found to parasitize *Heterodera glycines* eggs and cysts present in pots when the pots were inoculated with pelleted fungus or rice grain cultured inoculum. In petridishes, within 10 days, about 54% and 50% of the eggs in cysts were parasitized at 20° C. and 25° C., respectively, less were parasitized at 15° C. or 28° C., and approximately 2 to about 25% more larvae emerged in fungus treated dishes.

When the substantially pure culture of Arkansas Fungus 18-A was tested against *Meloidogyne incognita*, the test resulted in 30% of *Meloidogyne incognita* eggs being diseased. In this experiment, the Arkansas Fungus 18-A was pelletized and put in soil infected with *Meloidogyne incognita*. To this end the substantially pure culture of Arkansas Fungus 18-A were used at 5, 10, 15 or 20 grams of a substantially pure culture.

Also for the control of *Meloidogyne incognita*, PF-5 g (5 grams of a substantially pure culture of pelleted Arkansas Fungus 18-A) was mixed with *Arthrobotrys dactyloides* (AD-5 g) or *A. arthrobotryoides*, (AA-5 g) and tested on 'California Wonder' pepper in sterilized soil. The Arkansas Fungus 18-A treated pepper plants had much better growth than the control but the number of egg masses was not significantly different.

In tests against *Heterodera glycines*-inoculated 'Lee' soybeans the tests utilizing the substantially pure culture of Arkansas Fungus 18-A had fewer females and eggs in fungus treated soil than the control. It was also found that a composition of 15 grams of the substantially pure culture of Arkansas Fungus 18-A pelleted fungus plus 10 grams of cornmeal or 25 grams of the substantially pure culture of Arkansas Fungus 18-A was better than 15 grams of the substantially pure culture of Arkansas Fungus 18-A alone. *Heterodera glycines* females were reduced 99, 88, and 76%, respectively, by the three treatments. 15 g of the pelleted fungus applied 1 week pre-plant and at-plant was more effective than 1 week post-plant. A mycelium suspension (of Arkansas Fungus 18-A) was less effective.

The above tests demonstrate that the substantially pure culture of Arkansas Fungus 18-A is a useful biocontrol agent against *Heterodera glycines* and *Meloidogyne incognita*.

The following, hypothetical examples illustrate how the method of the present invention can be used to control nematodes in crops.

EXAMPLE 1

A substantially pure culture of Arkansas Fungus 18-A is made into a pelleted form. The pelleted product is applied to the soil, much as a fertilizer would be applied, at the time of planting of the crop. The pelleted fungus is applied at a rate of about 600 pounds per acre as a row treatment. Based on greenhouse studies and observations of naturally infested soil an approximately 90% reduction in nematode numbers would be expected. Except in soils with very high populations, a 90% reduction in nematode population will reduce damage by soybean cyst nematode to an undetectable level.

EXAMPLE 2

A substantially pure culture of Arkansas Fungus 18-A is chopped into small pieces and suspended in water. The fungal suspension is fed into an irrigation pipe and applied to a field by overhead irrigation at a rate of 500 pounds of mycelium per acre.

Flood irrigation, however, is not as effective because the fungal mycelium may settle out too near the water source. Overhead irrigation will provide a more uniform distribution over the entire field. There is no danger in utilizing an air application because the fungus does not affect soybeans or any other plants that have been tested.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for controlling crop pests and parasites comprising the step of treating a crop with a sufficient quantity of a substantially pure culture of Arkansas Fungus 18-A so as to control the pests.

2. The method of claim 1 wherein the substantially pure culture of Arkansas Fungus 18-A is applied in pellet form.

3. The method of claim 1 wherein the substantially pure culture of Arkansas Fungus 18-A is applied through an irrigation process.

4. The method of claim 1 wherein the pests that are controlled are nematodes chosen from the group consisting of *Heterodera glycines*, *Meloidogyne incognita*, and *Heterodera schachtii*.

5. A method of controlling certain nematodes on crops comprising the step of treating the crop with a composition containing a substantially pure culture of Arkansas Fungus 18-A at the time of planting.

6. The method of claim 5 wherein the substantially pure culture of Arkansas Fungus 18-A is applied in pellet form.

7. The method of claim 5 wherein the substantially pure culture of Arkansas Fungus 18-A is applied through an irrigation process.

8. The method of claim 5 wherein the pests that are controlled are nematodes chosen from the group consisting of *Heterodera glycines, Meloidogyne incognita*, and *Heterodera schachtii.*

9. A method of controlling *Heterodera glycines* in a soybean crop comprising the step of treating the soybean crop with a sufficient quantity of a substantially pure culture of Arkansas Fungus 18-A.

10. The method of claim 9 wherein the substantially pure culture of Arkansas Fungus 18-A is applied in pellet form.

11. The method of claim 9 wherein the substantially pure culture of Arkansas Fungus 18-A is applied through an irrigation process.

* * * * *